(12) United States Patent
Hoffmann et al.

(10) Patent No.: US 10,093,954 B2
(45) Date of Patent: Oct. 9, 2018

(54) METHOD FOR THE SPATIAL ARRANGEMENT OF SAMPLE FRAGMENTS FOR AMPLIFICATION AND IMMOBILIZATION FOR FURTHER DERIVATIZATIONS

(71) Applicant: ALBERT-LUDWIGS-UNIVERSITAET FREIBURG, Freiburg (DE)

(72) Inventors: Jochen Hoffmann, Freiburg (DE); Guenter Roth, Freiburg (DE)

(73) Assignee: ALBERT-LUDWIGS-UNIVERSITAET FREIBURG (DE)

( * ) Notice: Subject to any disclaimer, the term of this patent is extended or adjusted under 35 U.S.C. 154(b) by 236 days.

(21) Appl. No.: 14/347,278

(22) PCT Filed: Oct. 1, 2012

(86) PCT No.: PCT/EP2012/069359
§ 371 (c)(1),
(2) Date: Mar. 26, 2014

(87) PCT Pub. No.: WO2013/045700
PCT Pub. Date: Apr. 4, 2013

(65) Prior Publication Data
US 2014/0228245 A1    Aug. 14, 2014

(30) Foreign Application Priority Data
Sep. 30, 2011   (DE) .................. 10 2011 054 101

(51) Int. Cl.
C12Q 1/68      (2018.01)
C12P 19/34     (2006.01)
C12Q 1/6837    (2018.01)

(52) U.S. Cl.
CPC ............ *C12P 19/34* (2013.01); *C12Q 1/6837* (2013.01); *B01J 2219/00317* (2013.01); *B01J 2219/00333* (2013.01); *B01J 2219/00641* (2013.01); *B01J 2219/00722* (2013.01)

(58) Field of Classification Search
None
See application file for complete search history.

(56) References Cited

U.S. PATENT DOCUMENTS

| | | |
|---|---|---|
| 5,795,714 A | 8/1998 | Cantor et al. |
| 6,017,738 A | 1/2000 | Morris et al. |
| 6,060,288 A | 5/2000 | Adams et al. |
| 6,274,351 B1 | 8/2001 | Peponnet |
| 6,300,070 B1 | 10/2001 | Boles et al. |
| 6,355,431 B1* | 3/2002 | Chee .............. C12Q 1/6813 435/6.11 |
| 6,514,768 B1 | 2/2003 | Guire et al. |
| 9,725,758 B2 | 8/2017 | Zengerle et al. |
| 2003/0232382 A1* | 12/2003 | Brennan ............ C12Q 1/686 435/6.18 |
| 2005/0048580 A1 | 3/2005 | Labaer et al. |

FOREIGN PATENT DOCUMENTS

| | | |
|---|---|---|
| EP | 1203945 B1 | 12/2006 |
| JP | 2001000183 A | 1/2001 |
| WO | 01/27327 A2 | 4/2001 |
| WO | 2006088876 A2 | 8/2006 |
| WO | 2006110855 A2 | 10/2006 |
| WO | 2008/022332 A2 | 2/2008 |
| WO | 2008022332 A2 | 10/2008 |
| WO | 2010/100265 A1 | 9/2010 |

OTHER PUBLICATIONS

Jochen Hoffmann et al: "Solid-phase PCR in a picowell array for immobilizing and arraying 100?000 PCR products to a microscope slide", in: Lab on a Chip, vol. 12, No. 17, Jan. 1, 2012, p. 3049-3054.
Jochen Hoffman et al.: "Single-Molecule PCR in a Picowell Array Simultaniously Immobilizing PCR Products to a PDMS Coverslide", in: 15th International Conference on Miniaturized Systems for Chemistry and Life Sciences Oct. 2-6, 2011 Seattle USA, Oct. 2, 2011, pp. 900-902.
Bing, et al., Bridge Amplification: A Solid Phase PCR System for the Amplification and Detection of Allelic Differences in Single Copy Genes, Genetic Identity Conference Proceedings (1996).
Blanchard, et al., Cheap DNA Arrays—It's Not All Smoke and Mirrors, Nature Biotechnology, vol. 17, pp. 953 (Oct. 1999).
Dec. 13, 2012 Office Action issued in U.S. Appl. No. 13/224,645.
He, et al., Printing Protein Arrays from DNA Arrays, Nature Methods, vol. 5, No. 2, pp. 175-177 (2008).
Hoffman, et al., "Single-Molecule PCR in a Picowell Array Simultaneously Immobilizing PCR Products to a PDMS Coverslide" 15th International Conference on Miniaturized Systems for Chemistry and Life Sciences., pp. 900-902, (Oct. 2-6, 2011).
http://www.cogenics.com/sequencing/service/pdf/titanium_lit.pdf, Genome Sequencer FLX System Workflow (2008).
http://www.techno-preneur.net/technology/new-technologies/life-sciences/novel.htm (2005).
Jan. 13, 2016 Office Action issued in U.S. Appl. No. 13/224,645.
Jan. 7, 2014 Office Action issued in U.S. Appl. No. 13/224,645.
Jul. 3, 2013 Office Action issued in U.S. Appl. No. 13/224,645.
Kane, et al., Patterning Proteins and Cells Using Soft Lithography, Biomaterials, 20, pp. 2363-2376 (1999).
Kim, et al., Parallel Fabrication of RNA Microarrays by Mechanical Transfer from a DNA Master, Analytical Chemistry, vol. 79, No. 23, pp. 8994-8999, (2007).

(Continued)

*Primary Examiner* — David C Thomas
(74) *Attorney, Agent, or Firm* — Agris & Von Natzmer, LLP; Joyce Von Natzmer (57) ABSTRACT

The invention relates to a method for performing a biochemical or chemical reaction for an isolated, spatially separated amplification of sample fragments during a simultaneous immobilization and spatial arrangement of the sample fragments and reaction products, the amplification products, on one or more suitable solid phases for subsequent derivatizations.

26 Claims, 6 Drawing Sheets
Specification includes a Sequence Listing.

(56) References Cited

OTHER PUBLICATIONS

Kim, et al., Transfer of Surface Polymerase Reaction Products to a Secondary Platform with Conservation of Spatial Registration, Journal of the American Chemical Society, vol. 128, pp. 12076-12077 (2006).

Mardis, et al., The Impact of Next-Generation Sequencing Technology on Genetics, Trends in Genetics, Elsevier Science Publishers B.V., vol. 24, No. 3, pp. 133-141 (2008).

Marguiles, et al., Genome sequencing in micro-fabricated high-density picolitre reactors, Nature, vol. 437, pp. 376-380 (2005).

Matsubara, et al., "On-Chip Nanoliter-Volume Multiplex TaqMan Polymerase Chain Reaction from a Single Copy Based on Counting Fluorescence Released Microchambers", Anal. Chem., vol. 76, 6434-6439 (2004).

Morozova, et al., Application of Next-Generation Sequencing Technologies in Functional Genomics) Genomics, 92, pp. 255-264 (2008).

Official Communication issued in corresponding Chinese Patent Application No. 201080019880.7, dated Apr. 26, 2013.

Official Communication issued in corresponding International Application PCT/EP2010/052849, dated Oct. 7, 2011.

Official Communication issued in International Patent Application No. PCT/EP2010/052849, dated Jun. 22, 2010.

Peng, et al., Recent Developments in the Fabrication of DNA Microarrays, Physics, vol. 32, No. 9, pp. 599-603 (2003).

Ramachandran, et al., On-Chip Protein Synthesis for Making Microarrays, Methods in Molecular Biology, vol. 328, pp. 1-14 (2006).

Shen, et al., "Digital PCR on a SlipChip" Lab Chip., pp. 2666-2672 (Oct. 21, 2010).

Shendure, et al., Next-Generation DNA Sequencing, Nature Biotechnology, vol. 26, pp. 1135-1145 (Oct. 2008).

Sundberg, et al., "Spinning Disk Platform for Microfluidic Digital Polymerase Chain Reaction"., Analytical Chemistry, vol. 82, No. 4, pp. 1546-1550 (2010).

Torres, et al., Gene Expression Profiling by Massively Parallel Sequencing, Genome Research, 11 pages, (http://genome.cshlp.org/content/18/1/172.full?sid=d7c2913f-aab2-45f5-8e10-681062e04f63#fn-group-1) (2008).

Voelkerding, et al., Next-Generation Sequencing: From Basic Research to Diagnostics, Clinical Chemistry, 55:4, pp. 641-658 (2009).

Wolfram, et al., Reach-Through Claims und . . . Reach-Through Licensing -Wie Weit Kann Patentschuz auf biotechnologische Research Tools Reichen?, Mitteilungen der deutschen Patentanwälte, pp. 57-64, (2003).

Yu, et al., Contact Printing Beyond Surface Roughness: Liquid Supramolecular Nanostamping, Advanced Materials, vol. 19, pp. 4338-4342 (2007).

* cited by examiner

METHOD FOR THE SPATIAL ARRANGEMENT OF SAMPLE FRAGMENTS FOR AMPLIFICATION AND IMMOBILIZATION FOR FURTHER DERIVATIZATIONS

CROSS-REFERENCE TO RELATED APPLICATIONS

This is the U.S. national stage of International application PCT/EP2012/069359, filed Oct. 1, 2012 designating the United States and claiming priority to German application DE 10 2011 054 101.2, filed Sep. 30, 2011.

The invention relates to a method for performing a biochemical or chemical reaction for an isolated, spatially separate amplification of sample fragments with simultaneous immobilization and a spatial arrangement of the sample and reaction products, the amplification products, on one or more suitable solid phases for subsequent derivatizations.

An amplification reaction is understood to refer to the synthesis of clonal copies (amplification products) of a defined starting material, which is, for example, DNA or RNA of various biological sources in purified and often fragmented form. The amplification products may thus be referred to as reaction products of the amplification reaction. Microcompartments consisting of an aqueous solution and surrounded by oil are often created to perform the amplification in the prior art. This so-called oil-in-water emulsion allows a spatial and chemically reactive separation of the microcompartments. The microcompartment contains a microbead coated with capture molecules, an amplification mix and exactly one sample fragment. Up to $10^7$ identical DNA copies of a sample fragment are created in the course of the amplification reaction and are bound to the surface of the microbead. If the amplification mix is a PCR mix (PCR=polymerase chain reaction), then this process is known as oil emulsion PCR (emPCR) [Dressman et al., Proc. Natl. Acad. Sci. USA, vol. 100, pp. 8817-8822, 2003].

The basic concept of performing enzymatic amplification reactions in emulsions was described for the first time by Griffiths and Tawfik in 1998 [Tawfik Biotechnol, vol. 16, pp. 652-656, 1998]. This concept was used in 2003 and 2004 to permit amplification of DNA sample fragments by means of PCR in oil emulsions [Nakano et al., Journal of Biotechnology, vol. 102, pp. 117-124, 2003] or for simultaneous immobilization of the DNA amplification products on a microbead [Dressman et al., Proc. Natl. Acad. Sci. U.S.A., vol. 100, pp. 8817-8822, 2003; Nakano et al., Journal of Bioscience and Bioengineering, vol. 99, pp. 293-295, 2005; Musyanovych, Mailander and Landfester, Biomacromolecules, vol. 6, pp. 1824-1828, 2005; Diehl et al., Nature Methods, vol. 3, pp. 551-559, 2006]. Microbeads here refer to monodisperse (identical size) polymer beads in the usual size range of 10 nm to 100 μm. The surface of the microbeads may be activated, so that preferably capture molecules but also amplification products can be immobilized. The functionality of both bound capture molecules and amplification products should remain as unrestricted as possible.

The smallest compartmentalization in which PCR was demonstrated was in liposomes (V=3.3 aL) [Oberholzer, Albrizio and Luisi, Chemistry & Biology, vol. 2, pp. 677-682, 1995] and water-in-oil emulsions (V=1 aL) [Musyanovych, Mailander and Landfester, Biomacromolecules, vol. 6, pp. 1824-1828, 2005; Diehl et al., Nature Methods, vol. 3, pp. 551-559, 2006; Zeng et al., Anal. Chem., vol. 82, pp. 3183-3190, 2010; Novak et al., Angewandte Chemie—International Edition, vol. 50, pp. 390-395, 2011]. However, it is impossible to achieve a defined arrangement of the reaction compartments according to this method. This can be accomplished at the soonest following the reaction by arranging the microbeads.

It is known from the prior art that the totality of microbeads in a separate step can be brought into a regular arrangement on a surface/carrier material. This can be accomplished, for example, by introducing the microbeads into a multiwell array, for example, the systems GS FLX, GS FLX Titanium, GS Junior and PGM—personal genome machine—or by immobilizing the microbeads on a planar surface by means of systems that are available commercially, for example, SOLiD and G.007 Polonator. By means of a subsequent derivatization, for example, a sequencing reaction, a certain nucleic acid sequence can be assigned to each position of a microbead.

The spatial separation of microcompartments for amplification reactions is currently implemented mainly by two systems. In addition to the compartmentalization in microbeads, e.g., in emPCR which separates individual reaction phases by oil phase, separation in microcavities is also described in the prior art, where, for example, individual amplification regions are separated from one another by a solid phase.

In the last two decades, systems have been described which have investigated a PCR within a microstructured solid phase, a microfluidic chip (on-chip microreactors), in corresponding microcompartments in reaction volumes of up to 1.3 pL [Leamon et al., Electrophoresis, vol. 24, pp. 3769-3777, 2003; Dube, Qin and Ramakrishnan, PLoS ONE, vol. 3, 2008; Marcus, Anderson and Quake, Anal. Chem., vol. 78, pp. 956-958, 2006; Matsubara et al., Bioelectron., vol. 20, pp. 1482-1490, 2005; Shen et al., Lab Chip, vol. 10, pp. 2666-2672, 2010; Nagai et al., Anal. Chem. 73, 2001, pp. 1043-1047]. These compartments allow compartmentalization and amplification of DNA but these compartments are not filled individually. Therefore it is impossible to simultaneously test different samples and to assign the corresponding amplification products to the corresponding samples. Such an on-chip PCR is described in the disclosure by Mitterer et al. ("Microarray-Based Identification of Bacteria in Clinical Samples by Solid-Phase PCR Amplification of 23S Ribosomal DNA Sequences", Journal of Microbiology, March 2004, p. 1048-1057) where solid-phase primers may also be used. Here again, however, it is impossible to apply different samples to the individual spots. This array is filled through one opening so that the sample fragments are distributed over the individual spots. It is therefore impossible to make an assignment between amplification product and original. It is only possible to detect which amplification products were produced.

Practical handling and analysis of individual molecules are often referred to as digital PCR within the context of detection of individual DNA fragments [McCaughan and Dear, J. Pathol., vol. 220, pp. 297-306, 2010; Zhang and Da, Chem. Rev., vol. 110, pp. 4910-4947, 2010; Fair, Microfluid. Nanofluid., vol. 3, pp. 245-281, 2007]. Digital PCR is understood to be a special case of PCR in on-chip microreactors where precisely one or only a few sample fragments are amplified per microcompartment, in particular precisely one or only a few different DNA molecules are amplified. If a DNA molecule is present, a specific amplification product is formed. This method makes it possible to detect individual identical DNA molecules in the form of a digital count of the positive amplification reactions and/or of the corresponding positive microcompartments. This is known as digital PCR (dPCR) because the amplification reaction is based on PCR.

The first dPCT in a microstructured chip as an array of microcompartments was described in 2004 by Matsubara et al. [Matsubara et al., Anal. Chem., vol. 76, pp. 6434-6439, 2004]. Additional publications described dPCR in microreactors [Shen et al., Lab Chip, vol. 10, pp. 2666-2672, 2010; Sundberg et al., Anal. Chem., vol. 82, pp. 1546-1550, 2010]. By means of dPCR the number of DNA molecules in a sample solution can be determined with a high precision [Hirono-Hara, Noji and Takeuchi, J. Appl. Phys., vol. 105, pp. 102016-5, 2009; Bhat et al., Analytical and Bioanalytical Chemistry, vol. 394, pp. 457-467, 2009]. This can also be used to determine the DNA concentration in sequencing [Dube, Qin and Ramakrishnan, PLoS ONE, vol. 3, 2008; White et al., Bmc Genomics, vol. 10, pp. 116, 2009]. In addition, dPCR can be used for detecting highly parallel gene expression [Fan and Quake, Anal. Chem., vol. 79, pp. 7576-7579, 2007; Warren et al., Proc. Natl. Acad. Sci. U.S.A., vol. 103, pp. 17807-17812, 2006]. As is also done in PCR in on-chip microreactors, amplification of individual sample fragments also takes place in digital PCR, but there is no immobilization of the amplification products. It is also a disadvantage that dPCR is time consuming and is associated with high costs.

The possibility described here for amplification of sample fragments, for example, nucleic acid sequences, is an upstream reaction if today's sequencing methods (next generation sequencing systems) are used for detection of nucleic acid sequences, for example. In such sequencing methods, the amplification products produced in the amplification reaction are derivatized.

U.S. Pat. No. 6,300,070 describes a method for amplification of individual DNA molecules on surfaces where the DNA molecules are bound covalently at one end to surface-bound DNA capture molecules. The second end of the DNA molecule is then attached to a neighboring DNA capture molecule. Therefore, in these reactions, individual sample fragments are locally amplified and spatially immobilized (also referred to as bridge amplification). However, there is no physical subdivision into compartments, so that it may happen that the amplification regions run into one another and thus two or more regions may overlap. Therefore, the amplification products cannot be assigned to a certain sample fragment with sufficient reliability. Another disadvantage is that only the resulting strand and mating strand can be immobilized. It is impossible to bind just one strand.

WO 2009/0127589 describes a method and a device for sequencing DNA based on an FET array for calorimetric determination of an unknown DNA sample fragment. However, in this method the samples are not separated from one another during the actual reaction. Furthermore, the immobilization takes place outside of the chip in the form of oil emulsions. Therefore, the system described there is very complex and does not allow an unambiguous assignment of samples and amplification products.

U.S. Pat. No. 6,001,568 discloses a method for amplification of individual DNA molecules with simultaneous immobilization in a solid-state matrix that is gelatinous or is permeated with micropores. Sample fragments are deposited with a random distribution, so they are spatially separate from one another, then are amplified and immobilized. However, the disadvantage here is that the spatial separation is not retained during the reaction because the amplification regions expand and merge into one another, so that a subsequent unambiguous assignment of amplification products is impossible.

In addition, U.S. Pat. No. 6,482,593 describes a method and a device for detection of DNA molecules with the help of a sensor array. This array is a structured multiwell array having capture molecules (biosensors) immobilized in discrete locations. However, there is no amplification reaction.

U.S. Pat. No. 7,244,559 discloses a method for DNA sequencing. The sample fragments to be sequenced are aligned in several linear rows one after the other to obtain an amplified signal from a subsequent sequencing reaction. However, the amplification takes place in an upstream step outside of the array. This method is therefore complex and susceptible to errors.

U.S. Pat. No. 7,323,305 describes a method for sequencing DNA. The sample fragments are amplified by means of an emPCR in which the amplification products are amplified and immobilized on microbeads. However, it is impossible to amplify several individual samples in parallel and separately from one another. Another disadvantage is that no array with which subsequent analyses can be performed is created.

One disadvantage of this method described in the prior art is mainly that there is no spatially defined arrangement of microcompartments in relation to one another. A separate step would be necessary for this by bringing the microbeads into a defined arrangement relative to one another. Or a spatially defined arrangement of the microcompartments is possible but there is no immobilization of the amplification products. Commercial systems do not allow modification so that, for example, a master array could be produced.

U.S. Pat. No. 7,335,762 describes a method for sequencing DNA with the focus on redoubt of the sequencing reaction, wherein the sample fragment is bound to a mobile phase. This prior art is not satisfactory because no compartments into which different samples can be applied are provided. The amplification must also be performed upstream, which makes it even more time-consuming and expensive.

U.S. Pat. No. 7,638,276 describes a method for an emPCR for synthesis of DNA clones with simultaneous immobilization on microbeads for DNA sequencing. Here again, it is impossible to apply multiple samples side by side.

WO 2004/044240 describes a method for parallel detection of different nucleic acids in which primers are lengthened in the presence of nucleic acid and the primers have an intermediate section. This intermediate section is amplified by means of another primer pair and detected with a probe by hybridization. However, the number of DNA fragments that can be amplified and analyzed at the same time is limited. In particular it is impossible to establish an unambiguous assignment between the sample nucleic acid and the resulting amplification product. It is only possible to detect that a certain amplification product has been formed.

WO 2009/156915 describes an amplification method which permits detection of the amplification products. The amplification products are bound to capture molecules but this is not covalent bonding so the bonding comes about only at certain temperatures and does not persist permanently. It is thus possible to detect only that a certain product has been formed. After detection, however, the amplification product is back in solution and is not available for the subsequent analyses. Therefore no array can be established. Furthermore, an unambiguous assignment between the product and the starting molecule is impossible when using several starting molecules.

It is known from the disclosure by Mikhailovich et al. ("Identification of Rifampin-Resistant *Mycobacterium Tuberculosis* Strains by Hybridization, PCR, and Ligase Detection Reaction on Oligonucleotide Microchips" J. of Clinic. Microbiology, 2001, pp. 2531-2540) that capture molecules can be immobilized in gel. Here again, however, an unambiguous assignment of the amplification products and the corresponding samples is impossible because the amplification products are not initially free in solution and they may diffuse toward spatially remote capture molecules.

The next generation sequencing systems described in the prior art have numerous disadvantages. Firstly, these systems require amplification of the sample fragments before the actual sequencing process, and secondly, they require a spatial fixation of the amplification products to obtain a discrete signal of the sequencing reaction. The compartmentalization and amplification of individual sample fragments are achieved by emPCR in a first separate step. The regular arrangement of the amplification products on a solid phase is achieved in a second separate step by spatial fixation of the microbeads on a surface. The emPCR process is very complex and is associated with a loss of sample fragments. This definitely restricts the analysis of mixtures of sample fragments, which contain only a few identical copies of each sample fragment in particular (low redundancy of the sample). This is true in particular of single cell analyses. In commercial systems such as GS FLX, GS FLX Titanium, GS Junior, SOLiD, PGM—Personal Genome Machine—and G.007 Polonator, the amplification products of the sample fragments are synthesized by emPCR and, in the process, are immobilized on the surface of beads (microbeads) [A. Griffiths and D. Tawfik, U.S. Pat. No. 7,638,276]. Next, the purified beads are affixed to the surface for sequencing by various mechanisms in a regular arrangement on the surface. There are disadvantages to performing emPCR, some of which are due first of all to the cost of DNA beads (capture beads for immobilization of sample fragments), magnetic beads (enrichment beads required for purification after emPCR) and chemicals (detergents, buffers, emulsion oil, emPCR reagents). Secondly, special laboratory equipment is required for handling the beads. Such equipment includes particle counters/counting systems for quantifying the purified beads after emPCR. The time for performing an emPCR process is 11 to 13 hours, which is a disadvantage of the known systems. One explicit disadvantage of the emPCR process is that the amplification and immobilization efficiency depend on the length of the sample fragments. The longer the sample fragment, the longer must be the holding time set for the individual temperature steps for PCR. As a result, the probability for fusion of individual oil droplets is greatly increased in particular at high temperatures around 95° C. However, melting the droplets dissolves the compartmentalization, which in turn leads to a loss of "pure" sample fragments because then at least two sample fragments are combined. As a result, only a very few pure amplification product microbeads are available after the end of the process. Therefore, a length of approximately 500 base pairs is the current limit with DNA.

In sequencing systems which use bridge amplification, there is no need for emPCR because the amplification takes place directly on a surface coated with capture molecules. The disadvantage of this system is that the individual amplification product regions can grow and can thus grow into one another. Therefore, complete compartmentalization is not ensured. In addition, another disadvantage is that both the sense and antisense DNA strands are immobilized on the surface in bridge amplification. This yields a mixture of the two DNA strands.

In systems for digital PCR, a spatial compartmentalization of the sample fragment is also achieved after amplification of the amplification product by a microfluidic system. In general, only a single sample fragment or just a few sample fragments are immobilization of the amplification product and simultaneous spatially defined arrangement thereof are not described for digital PCR.

In addition, contamination often occurs in the methods and systems disclosed in the prior art because the compartments are only inadequately sealed with respect to one another. Furthermore, the disclosed systems cannot be supplied by mass production methods and furthermore, they are not compatible with other biomolecules. Use of these systems is limited exclusively to DNA.

The object of the present invention is therefore to create a new amplification method which does not have the disadvantages and shortcomings of the prior art.

DESCRIPTION

The object is achieved by the independent claims. Advantageous embodiments are derived from the dependent claims.

Methods of amplification of sample fragments comprising the following process steps:
  a. Supplying a solid phase with a microstructure, wherein the microstructure subdivides the solid phase so that at least one, preferably multiple compartments are formed and capture molecules are attached to the solid phase,
  b. Introducing at least one sample fragment into at least one compartment,
  c. Introducing a reaction mixture for amplification into at least one compartment,
  d. Separating and/or covering the individual compartments,
  e. Amplification step wherein each sample fragment is amplified independently in the corresponding sealed compartment,
  f. wherein the amplification product generated by the amplification step are immobilized on the capture molecules.

The method according to the invention is advantageous in comparison with the prior art because amplification of the individual sample fragments takes with simultaneous immobilization of the amplification products. This occurs through regular arrangement of the capture molecule on a solid phase, which thus makes it possible to bypass emPCR, for example, and spatially separate amplification and arrangement of sample fragments is achieved directly. A fragmented sample is introduced into the microstructured solid phase. Microstructuring and/or microstructure in the sense of the invention refer(s) in particular to a structuring of the surface of the solid phase in the nanometer range or the micrometer range. A solid phase in the sense of the invention refers in particular to a solid carrier in which or on which the amplification reaction takes place.

The solid phase preferably has at least one compartment. It is preferable for the compartments to be designed as microcompartments which are compartments in the micrometer range in the sense of the invention. The solid phase preferably has a plurality of microcompartments, and it is preferable that the plurality of compartments each contains exactly one type of sample fragment. In other words, it is preferable that fragments of a sample are contained in a compartment so that the solid phase in particular the compartments may contain fragments of numerous identical or different samples.

Capture molecules are bound to the microstructured surface of the solid phase. It may be preferable for the surface to also bind additional molecules in particular the amplification products. It is especially preferable that the capture molecules are bound to the surfaces in the compartments. This embodiment yields particularly good results because this ensures that as many capture molecules as possible can bind to the amplification products and thus a high density of bound amplification products is obtained.

The method according to the invention is characterized in particular in that each compartment can be filled separately and there is not just one filling port, so that the sample fragment is distributed among the various compartments. This offers a number of possibilities because now a high number of samples can be amplified and analyzed in parallel.

Furthermore, it may be preferable that the reaction mixture, preferably an amplification mix is introduced before the sample fragment. Those skilled in the art will know which order is the best for the respective reagents and applications without having to make an inventive step himself.

Furthermore, the invention is characterized in that each sample fragment is amplified separately in its compartment and there cannot be any mixing or overlapping of the amplification regions during the reaction. The strict spatial separation of the samples is thus preserved, even during the reaction, at least to amplification products that are spatially separated from one another. The amplification products provided in this way may also be referred to as products of the amplification step or of the amplification reaction in the sense of this invention.

In the present invention an amplification product refers in particular to the totality of all the images of a single sample fragment prepared by an amplification reaction. It is preferably an identical or unambiguously derivable derivative of the sample fragment. The amplification product or subsections of same may be derived from one or more subsections or from the totality of one or more sample fragments. If, for example, genomic DNA is used for an amplification reaction, in particular PCR for a preferred method, an amplification product with an identical sequence is obtained, but this is only a subsection of the genomic DNA. If modified dNTPs are used in particular here, then the amplification product is not molecularly identical but instead is only identical in sequence to the original DNA. If subsections of individual genes are joined by means of a "linkage PCR" then the amplification product is derived from a plurality of sample fragments, for example. The amplification product may advantageously also belong to a class of molecules that are different from the original molecule. All these products or images are amplification products in the sense of the invention.

It is preferable that an amplification product is amplified and thus additional amplification products are created. A particularly good saturation of the capture molecules can be achieved in this way, so that a high number of bound amplification products is obtained for the subsequent analyses.

In the sense of this invention, PCR refers to a polymerase chain reaction, which is an enzymatic reaction that is preferably controlled by temperature and is capable of producing an amplification product of an available DNA (sample fragment). The amplification step in the method according to the invention is preferably PCR.

The amplification products are immobilized on the capture molecules in their compartment so that there cannot be any mixing of the amplification products after the reaction. This permits a subsequent unambiguous assignment of the amplification product and the corresponding sample.

Through the present invention it is thus possible to amplify a variety of sample fragments, so that each fragment can be amplified separately in space and the separation can be maintained as far as the product level (=amplification product level).

It is especially preferable for the compartments to be cavities. It was completely surprising that advantageous effects could be achieved by introducing sample cavities in comparison with planar surfaces. The loss of sample in application was thus reduced substantially. There was also significantly less contamination. Furthermore, mixing of the sample fragments or the resulting amplification products is completely prevented by the cavities, but in the case of planar surfaces this represents an additional source of error. Due to the improved handling achieved through the use of cavities, this method can be used as a bulk method.

The cavities of the filled solid phase, preferably the filled multiwell arrays are compartmentalized by various methods, for example, and are isolated from one another in particular. Each method for compartmentalization is created, so that it permits the desired reaction and suppresses unwanted reactions or inhibitions.

It was completely surprising that it would be possible with this method to perform an independent biochemical and/or chemical reaction in the individual compartments. This not only makes it possible to easily and efficiently conduct high throughput methods but also significantly minimizes the risk of contamination.

The binding and/or immobilization of the amplification products to the surface of the respective microcompartments during the amplification reaction makes it possible to keep the amplification products largely separate from one another in subsequent reactions or analyses. This is important in particular if the microcompartments are opened to perform a further analysis or for derivatization of the amplification products (for example, sequencing). Furthermore, it is advantageously possible to select which region of the amplification products is bound, for example, the sense strand or the antisense strand or both in the case of DNA. The production costs as well as the consumption costs can be reduced substantially by this method because, for example, this permits savings in the cost of DNA beads (capture beads), magnetic beads (enrichment beads which are required for purification after emPCR) and chemicals (detergents, buffers, emulsion oil, emPCR reagents). In addition, it is advantageous that the process management is simplified. The individual process steps can be performed by less trained personnel and do not require special expertise that must be learned, such as that required for performing the amplification and purification of the amplification products in the method described in the prior art. Another advantage of this method is that standard laboratory equipment such as incubators, heating and cooling equipment, centrifuges or vacuum support and pipettes, for example, are required. No expensive or high-maintenance special instruments such as Coulter counters are needed. This method can be described as extremely simple, efficient and not susceptible to errors.

The faster processing time can be mentioned as another advantage in comparison with the prior art. For example, less time is required to perform the amplification. In a preferred embodiment of the method, it is possible, for example, to supply sequencing chips, preferably including all working steps such as preparation of the reaction mixture, introduction of the sample fragments and the amplification mix, covering, performing the reaction and washing after the reaction, preferably in 5 hours, whereas all the methods disclosed in the prior art require more than 11 hours.

Furthermore, a high efficiency and longer amplification products can be achieved. In a preferred embodiment of the method, it is thus possible to obtain very long amplification products of more than 10,000 bases (nucleic acid bases) on a microstructured solid phase. The amplification and immobilization of sample fragments with lengths of more than 500 base pairs should be emphasized in particular. The methods of the prior art, such as emPCR, are greatly limited because of the longer cycle times, which increases the risk of droplet fusing and thus slowing and/or inhibition of the process.

The invention may be regarded as a combination invention. The combination of the known elements in a microstructured solid phase leads to surprising effects in the amplification of sample fragments. It was thus completely surprising, for example, that the method for amplification of numerous molecules could be used and could be used universally in this way. Furthermore, the method can be performed rapidly and easily either manually or automatically. Only the combination of the individual process steps which are not known from the prior art leads to synergistic advantages which result in efficient amplification and immobilization of molecules.

In another preferred embodiment, the amplification products are analyzed, sequenced and/or derivatized following step f). A number of analyses may follow the method thanks to the spatial separation of the amplification products as well as the unambiguous assignment to the corresponding sample. Sequencing is especially advantageous here. A preferred embodiment involves the production of derivatives, for example, proteins.

It is preferable for the capture molecules to comprise short nucleic acid sequences. In a particularly preferred embodiment, the capture molecules are primers, most especially preferably primers that are used for the amplification step. Thus, in addition to the reaction primers, which are present in the reaction mixture, another primer group may be used as the capture molecule. It is particularly advantageous that at least one of the reaction primers is used as capture molecules. These primers are then immobilized on the solid phase, so that the amplification reaction takes place directly on the immobilized primer (capture molecule). In other words, in this embodiment, both the sample fragments and the amplification products are bound by the capture molecules. In this way, costs and time may be saved, among other things. Furthermore, the binding density also increases, which facilitates the subsequent analyses.

It is also preferable that methods in which the sample fragments and/or amplification products are immobilized on the capture molecules by covalent bonds are used. This ensures that the binding is also preserved, for example, in the elongation phase of amplification and is not released again at higher temperatures. For bound amplification products, this embodiment also means that these products are bound in a more stable form and the binding is therefore more durable, which facilitates subsequent analyses or reactions.

In another preferred embodiment, the invention relates to the method, whereby the introduction of the sample fragment and the introduction of the reaction mixture are performed in one step, preferably by mixing the sample fragment with the reaction mixture prior to introduction. Additional time may be saved by this procedure, depending on the structure of the solid phase.

A reaction mixture in the sense of the invention refers in particular to the totality of all molecules which make it possible to produce amplification products from a sample fragment. The composition of the mixture defines unambiguously which sample fragments will be amplified and in which way. A reaction mixture for RNA would be a mixture which contains an RNA polymerase, for example. A reaction mixture is preferably an amplification mix.

Furthermore, it is preferable for the reaction mixture and/or the sample fragment to be added by centrifugation, vacuum, atomization, immersion, dip coating and/or painting the surfaces of the solid phase. These methods are particularly suitable because the filling takes place in a time-saving manner and a high accuracy is ensured.

In a preferred embodiment, the microstructured solid phase is a surface having at least one individual compartment, preferably a plurality of separate individual compartments. The solid phase may be a multiwell array in particular. A multiwell array in the sense of the invention refers to a spatial arrangement of microcompartments, preferably cavities in particular. A reaction mixture can be placed in the cavities, and independent amplification reactions can take place within a microcompartment. It is preferable it there is no exchange of amplification products and/or sample fragments between the microcompartments of a multiwell array.

It may be preferable for the method to be used for supplying amplification products for a sequencing chip, wherein the solid phase is designed in particular as a multiwell array, preferably comprised of a regular arrangement of glass fibers structured on one side. In addition, the cavities may advantageously consist of a multilayer composite or track-etched membranes. The multiwell array preferably has 1-1000 cavities with individual volumes between 1 fL and 1 mL. The multiwell array may preferably be a multifiber array with optical fibers as the basic unit. These optical fibers are optical glass fiber bundles, for example, which advantageously make it possible to perform the preferred method at a high processing throughput.

Multiwell array refers in particular to a microstructured solid phase, preferably a surface containing sealable recesses. A multiwell array also comprises a chip which contains cavities.

The multiwell array preferably has a regular arrangement of hexagonal cavities. It has been found that hexagonal cavities are advantageous for automation of the process in particular, and the cavities can therefore be filled more rapidly.

In a preferred embodiment, the entire cavity or regions of the cavity or just the walls of the cavity are coated with metals, metal oxides or plastics.

Metals denote in particular chemical elements corresponding to the nomenclature of the Periodic Table of Elements (which, unlike the nonmetals in the periodic system, are to be found at the left of the diagonal dividing line beginning with the element beryllium (group 2) to the element polonium (group 16) as well as their alloys and intermetallic compounds, which have characteristic metallic properties.

Alternatively or additionally, at least one surface of at least one solid phase may be coated with nonmetallic materials. In a preferred embodiment, polymers may be used for the nonmetallic materials. According to the IUPAC definition (The International Union of Pure and Applied Chemistry), polymers are substances comprised of a group of chemically uniform macromolecules (polymer molecules), which differ with regard to the degree of polymerization, the molecular weight and chain length. In so-called uniform polymer substances, all the macromolecules have the same structure and differ only in their chain length (degree of polymerization). Such polymers are known as polymer homologs. Polymers may include inorganic polymers, fully or partially aromatic polymers, homopolymers, copolymers, biopolymers, chemically-modified polymers and/or synthetic polymers. Preferred polymers include, for example, polyethylene, polypropylene polyvinyl chloride, polystyrene, polymethyl methacrylate, polyamide, polyester, polycarbonate, polyethylene terephthalate, polyethylene glycol, dendrimers or silicones. Polymers can be selected from the group comprising inorganic polymers, organometallic polymers, fully or partially aromatic polymers, homopolymers, copolymers, biopolymers, chemically modified polymers and/or synthetic polymers and include polyethylene, polypropylene, polyvinyl chloride, polystyrene, polymethyl methacrylate, polyamide, polyester, polycarbonate, polyethylene terephthalate, polyethylene glycol, dendrimers, silicones, proteins, DNA, RNA, carbohydrates or polyhydroxyalkanoates.

It may be preferable to coat a surface with carbon, in particular carbon fibers or graphite fibers. It may also be preferable to use a coating of plastic. Plastics in the sense of the invention refer in particular to materials whose essential components consist of such macromolecular organic compounds that are formed synthetically or by modification of natural products.

For a preferred coating, plastics from the group of modified natural substances, synthetic plastics (polycondensates, polymerisates, polyadducts), thermoset plastics and/or unsaturated polyester resins.

It may be preferable to coat the walls of the cavities with titanium. It was completely surprising that more efficient binding of the capture molecules could be achieved by means of a titanium coating. Furthermore, because of the advantageous surface properties of titanium, adhesion forces are lower, so that there are fewer nonspecific interactions between the surface and the reaction components, and washing steps can also be performed more rapidly. In addition, it has been found that by means of the titanium coating, it is possible to suppress optical crosstalk in the sequencing reaction, for example, in the GS system from Roche, in which photons are released on incorporation of nucleotides and then are sent to the detector through optical fibers.

The surface may also be a planar surface containing a structuring or coating of hydrophobic and/or hydrophilic regions. Hydrophilic in the sense of this invention means in particular "loving water" whereas hydrophobic denotes in particular "avoiding water." The surface may be structured completely with a hydrophilic or hydrophobic coating in some regions. A hydrophobic or hydrophilic substance may also be applied to the surface. Hydrophobic substances preferably include fats, waxes or alcohols with long alkyl radicals or special coatings such as Teflon carbon black, for example. Hydrophilic substances include in particular salts or polar compounds or special coatings such as VISTEX.

The surface in another preferred embodiment may be a three-dimensional microstructure containing individual regions that can be separated from one another by suitable process management to form compartments, for example, small column at the tip of which the amplification takes place. It may also be advantageous to design the surface to be planar and unstructured so that it is sealed with a cover or some other closure means such as a coating, for example, so that the compartments are created.

The solid phase, in particular the multiwell array, is preferably made of different materials (semiconducting, amorphous, crystalline, fibrous). The cavities are preferably implemented by etching methods, among others, for example, by dry etching/reactive methods (including DRIE, the Bosch process, ICP), wet chemical methods (including bases, acids, HF) or physical methods (including drilling, sputtering, ionic etching). The solid phase, preferably the multiwell array may preferably contain any coatings, especially with metals, metal oxides or plastics. The cavities preferably have a different geometry selected from the group comprising square, rectangular, round, oval, triangular, hexagonal, octagonal, polygonal or combinations thereof. Furthermore, the cavities may advantageously have different depths and/or feature ratios (in particular dimensions). The cavities are advantageously arranged in different configurations relative to one another (regular or irregular).

Depending on the number of sample fragments introduced into the amplification system, preferably between 1 and 1000 fragments are introduced into the solid phase, preferably the multiwell array. In addition, each cavity may contain in particular between 1 and 10 fragments.

In another preferred embodiment, the invention relates to the method wherein the covering and/or separation of the compartments comprises oil, electric forces, phase transitions, inert regions and/or covers. A single cover is especially preferably used to cover all the cavities of a solid phase. This embodiment is advantageous because handling is facilitated and thus a rapid and effective covering of all cavities is achieved.

The cover may be made, for example, of different materials such as glass or polymers, in particular polydimethylsiloxane (PDMS), polypropylene (PP), cyclic olefin copolymers (COC) or cyclic olefin polymers (COP). The cover may be applied to the multiwell array after filling with the reaction or together with the reaction mixture. In addition, the cover may be pressed vertically onto the multiwell array or pulled horizontally over the multiwell array (slipping). It is preferable for the cover to contain capture molecules.

On closing the filled cavities, it is necessary to ensure that the amplification products cannot leave the amplification region. When using a cover, the wells are sealed by a purely mechanical method and the individual cavities are fluidically isolated from one another, which thus creates individual compartments for the amplification reaction. The material of the cover does not have an inhibiting effect on the reaction and is compatible with the amplification reactions.

Covers may also be coated with capture molecules. This embodiment leads to particularly surprising results. It is thus possible to separate the cover from the solid phase after conclusion of the reaction and to investigate it separately. The amplification products may thus be assigned unambiguously to the corresponding samples on the cover.

It is preferable for the cover to have the same or modified capture molecules to thereby bind the sample fragments, amplification products or derivatives of the amplification products. If the cover is equipped with different capture molecules than the solid phase, then other molecules may be immobilized in the cover, which entails advantageous properties, depending on the field of amplification.

The solid phase, preferably the multiwell array, may advantageously have different geometric embodiments. It is preferable for the cavities to be sealed by a closure means, a closure element or a cover and thus to be separated from one another spatially. In the sense of the invention, the terms "closure means", "closure element" and "cover" are used as synonyms. However, it may also be advantageous to use a liquid, for example, oil as the closure medium. Detergents may preferably be added to the oil.

The capture molecules may either be immobilized directly or indirectly on the solid phase. The capture molecule, preferably a nucleic acid, may contain a chemical coupling group or sequence on one or more ends. A coupling group or sequence is preferably attached to the 5' end. The coupling group or sequence may be, for example, biotin, double biotin, $NH_2$, SH, Acrydite and/or polynucleotide sequences.

Furthermore, it is preferable for the capture molecules to have at least one spacer molecule. This spacer is preferably situated between the coupling group and the nucleic acid sequence.

The length of the capture molecule is preferably not limited but is preferably between 1 and 1000 individual molecules or in the case of DNA, 1 to 1000 bases. These lengths yield especially good results with regard to the binding stability and specificity.

In another preferred embodiment, the invention relates to the method wherein the capture molecules comprise at least one binding site for sample fragments and/or amplification products.

It is also preferable that the capture molecules and/or the amplification products have a photoactivatable cleavage group. The photoactivatable group may be, for example, caged compounds such as photolabile nitrophenyl ethyl, 2-nitrobenzyl derivatives, coumarinyl derivatives, p-hydroxyphenacyl derivatives, benzoin derivatives, 1-acyl-7-nitroindoline derivatives. The capture molecule may be immobilized on a surface by means of the photoactivatable group. The photoactivatable group is cleaved under the influence of light or is chemically altered so that the amplification products immobilized by the capture molecules are decoupled from the surface in a targeted manner and made available for analyses.

It is especially preferable that the capture molecules contain a promoter binding site for an RNA polymerase or a cell-free expression system.

In another preferred embodiment, the invention relates to a method, wherein the capture molecules have a spacer molecule, contain a chemical coupling group at one or more ends and/or are thereby immobilized either directly or indirectly in the microstructured solid phase. The capture molecules are preferably short nucleic acid sequences. A spacer molecule is advantageously present between the coupling group and the nucleic acid sequence. A physical distance is created between the surface and the nucleic acid by introducing a spacer between a coupling group and a nucleic acid sequence. The spacer may consist of a carbon chain or a polynucleotide sequence (poly-T sequence), among other things.

The capture molecules preferably contain a chemical coupling group or coupling sequence on the 5' end of the nucleic acid, for example, at one or more ends for an oriented binding to a surface. This group is selected from the group comprising biotin, double biotin, amino groups ($NH_2$), thiol groups (SH), Acrydites, polynucleotiode sequences, streptavidine, His-Tag (His=histidine), nickel-NTA (NTA=nitrilotriacetic acid), myc- or flag-tag or combinations thereof.

The capture molecules are preferably immobilized directly or indirectly. Methods of direct immobilization of nucleic acids include another other things hydrogels, UV cros slinking, copolymerization in acrylamide gels, affinity bonds (avidine-streptavidine), ionic, absorptive or noncovalent bonds. Methods of indirect immobilization use linker molecules, preferably homobifunctional or heterobifunctional linker molecules to immobilize the capture molecules preferably at the surface of the cavities of the solid phase. Substances for immobilization include, for example, N,N'-diisopropylcarbodiimide (DIC), N-hydroxysuccinimide (NHS), melamido, NTMTA, N-(3-trifluoroethanesulf-ony-loxypropyl)anthraquinone-2-carboxamide (NTPAC), 4-(N-maleimidomethyl)cyclo-hexane-1-carboxylic acid 3-sulfo-n-hydroysuccinimide ester sulfo-n-hydroxysuccinimide ester (sulfo-SMCC), glycidyloxypropyltrimethoxysilane (GOPTS), trimethoxysilyil-propyl methacrylate (MPTS), methane thiosulfonate (MTS), 1-ethyl-3-(3-dimethyl-aminopropyl)carbodiimide (EDC), glutaraldehyde, N,N'-dicyclohexylcarbodiimide (DCC), Acrydite, silanized nucleic acids, phosphorothioate. The homobifunctional linker is preferably 1,4-phenylenediisothiocyanate (PDITC) and can be used in particular to coat the walls of the cavities with capture molecules with sequence lengths between 10 and 500. Binding of the capture molecules to a solid phase is preferably compatible with amplification reactions and possible subsequent derivatizations. In other words, the chemical, physical or biological binding of the capture molecules to the surface or a region of the surface does not have an inhibiting effect on the following reactions.

It is preferable for the capture molecules to comprise at least one binding site for sample fragments and/or amplification products and preferably to have a length of 1 to 1000 individual molecules. In the sense of the invention, capture molecules in particular denote molecular units which are bound to a solid phase and allow addition of amplified sample fragments or bind the amplification products. It was completely surprising that capture molecules which would specifically bind the amplification products and immobilize them could be made available. The purification of amplification products is greatly simplified in this way, such that the amplification products are available for additional reactions on the capture molecules.

It is preferable for the sample fragments to have adapters with a uniform sequence on at least one end. The preferred length of the adapters is between 1 and 1000 individual molecules. The adapters may have different functional units. Adapters are preferably present at the beginning and end of a sample fragment in the form of uniform and unambiguous sequences. They define the regions of the sample fragments that are amplified. The adapters function as primers for PCR in particular. One of the two adapters is advantageously identical entirely or in part to the sequence of the capture molecule. In the case of system for sequencing, the DNA to be sequenced has two defined adapters, usually predetermined by the manufacturer of the system. Either all of the totality of all sample fragments or only certain subunits of the totality can be amplified by means of the adapters. In addition, the adapters may preferably have several different functional units one after the other which may be in particular binding sites for RNA polymerases or cell-free expression systems. The adapter sequences may originate, for example, from conventional sequencing systems (including those from Applied Biosystems/Life Technologies, Ion Torrent/Life Technology, Roche, Illumina, George Church/Dover Systems) and may be identical in sequence or may contain additional sequences or modifications. The adapter sequences can thus create a surface capable of sequencing. A surface is capable of sequencing when amplified sample fragments have bound to the capture molecules. The amplification products are then available for additional investigations.

The promoter binding site lengthens the adaptor either at its one end or at the other or in and/or on any site on the capture molecule. The sequence of the capture molecules may be identical or partially identical to that of the sequencing systems such as, for example, with those from Applied Biosystems/Life Technologies, Ion Torrent/Life Technology, Roche, Illumina, George Church/Dover Systems. The sequence of the capture molecule is preferably a binding site for sample fragments, mediated in particular by the affinity of one of the adapters for the capture molecule. This sequence preferably lengthens the adapter at the 3' or 5' end. The adapters may contain one or more additional sequences on one or both ends, so that the sample fragments are lengthened by these special sequences during the reaction.

In a preferred embodiment, the sample fragments include nucleic acids, preferably DNA or RNA, proteins, antibodies, synthetic organic molecules, synthetic molecules, organic molecules and/or natural substances or they are released from cells or natural substances introduced into the compartments. A sample fragment is preferably a molecule that should be amplified. In the case of a cell, the sample fragment is released by a mechanism/reaction prior to amplification such as, for example, mechanical, chemical or thermal lysis. The totality of all sample fragments forms the sample. The sample fragments are preferably fragments of genomic DNA but may also be cDNA or RNA. The fragments may be created, for example, by shearing of genomic DNA as in the next generation sequencing, for example. The totality of sample fragments preferably consists of single-stranded and/or double-stranded nucleic acid sequences $(1-10^{10}$ base pairs (bp)), where each sample fragment preferably contains one or more adapter sequences (1 bp-1000 bp) at each end. The sample fragments may preferably be amplified or derivatized directly or indirectly by way of an incorporated label from DNA or RNA. It is preferable for the sample fragments to have a length of 1 to $10^{10}$, preferably $1-10^8$ individual molecules in a single-strand or double-strand form. The sample fragments may also be obtained from viruses, prokaryotes or eukaryotes or be of a synthetic nature. The length of a sample is preferably between 1 and $10^{10}$ individual monomers. Such samples can be subdivided into individual fragments by various methods. The fragments may be single- or double-stranded.

In a preferably embodiment the amplification step is selected in particular from the group comprising PCR, RPA, RCA, SDA, NASBA or LAMP. These abbreviations have the following meanings in particular: PCR stands for polymerase chain reaction, RPA 5 stands for recombinase-polymerase amplification, RCA stands for rolling circle amplification, SDA stands for strand displacement amplification, NASBA stands for nucleic acid sequence-based amplification, LAMP stands for loop-mediated isothermal amplification. However, the invention is not limited to these amplification possibilities.

The reaction mixture preferably comprises individual building blocks for the synthesis of the amplification products, an energy system, a synthesis system and 1 to $10^6$ different adapter sequences. The reaction mixture may in particular also be a standard commercial PCR amplification mix. The amplification step is preferably an isothermal amplification system. It may be preferable for sample fragments to be amplified with one or more amplification systems and immobilized in the cavities, for example. After the reaction, the multiwell array is washed, for example, with denatured sodium hydroxide (NaOH) to remove any unbound reaction products and to prevent contamination. The reaction mixture preferably contains a DNA polymerase in particular a Pfu or Taq polymerase and dNTPs or a mixture of dATPs, dCTPs, dGTPs, dTTPs and dUTPs and in particular a UNG digestive system. In addition, one to four adapters which have a sequence length between 10 and 500 nucleotides are preferably also included.

In the sense of the invention, the molecule dNTP (deoxyribonucleoside triphosphate) stands in particular for molecular monomers which are needed for synthesis of a DNA strand by means of an amplification system. It may be preferable for the sample fragment RNA to be available for amplifications so that in particular an RNA polymerase and comprising, instead of the dNTPs, dATP (deoxyadenosine triphosphate), dGTP (deoxy-guanosine triphosphate), dTTP (deoxythymidine triphosphate), dCTP (deoxycytidine triphosphate), the molecules dATP (deoxyadenosine triphosphate), dGTP (deoxy-guanosine triphosphate), dUTP (deoxyuridine triphosphate), dCTP (deoxycytidine triphosphate) are used.

It was completely surprising that it is possible with the preferred method to perform an amplification reaction and in particular to immobilize the amplification products thereby generated at the same time. It is preferable that an amplification step generates 1 to $10^{10}$ amplification products.

In a preferred embodiment, the reaction mixture contains components that improve the reaction. Reaction-improving components preferably include bovine serum albumin (BSA), agarose, tween, ultrasonically-treated nucleic acids and/or a UNG digestive system.

Amplification is preferably not emPCR. The generation of amplification products based on a sample fragment and arrangement of the amplification products on a surface are surprisingly linked to one another so that emPCT can be bypassed completely. It was completely surprising that the amplification of molecules in a solid phase would be possible, whereby the amplification products generated are bound by capture molecules. This method combines two steps, namely introduction of a fragmented sample into a spatially defined configuration of microcompartments and binding and/or immobilizing the amplification products on the surface of the respective microcompartments during the amplification reaction to keep the amplification products separate from one another in the following reactions or analyses. This yields surprising synergistic effects, such as time and cost advantages. The invention offers numerous advantages in comparison with the methods disclosed in the prior art so that time-intensive amplification reactions such as emPCR can be replaced.

In addition, the method permits microstructured surfaces to be coated with amplification products of sample fragments in a process that has local resolution, to then perform a derivatization or other amplification in addition to or instead of sequencing, and thus to also produce new products such as those that were not accessible with the previous method.

The invention also relates to a device for performing a method for amplification of sample fragments. A device for performing a reaction includes in particular a cassette which may hold, for example, a multiwell array and is brought to a state which promotes the enzymatic reaction of amplification. Good heat input counts as a method in particular in the case of using a temperature-controlled amplification system. The device preferably consists of a material such as plastic or metal which permits a good temperature control and is performed in a device which also permits good temperature control.

A device for performing an method according to the invention comprising the following steps is preferred:
g) a solid phase with at least one preferably multiple compartments, wherein capture molecules are bound to the surface of the solid phase, preferably to the compartments and
h) a separation and/or covering.

The device also prevents contamination with capture molecules and sample fragments because the cavities present in the cassette or multiwell array are completely covered by a cover so that reliable mechanical sealing of the cavities, for example, the multiwell array is achieved. Furthermore, the device has a filling device which permits easy filling of the individual compartments or cavities. The reaction device may be subject to a PCR temperature protocol.

This device may be referred to in particular as a front-end complement for the sequencing systems GS FLX, GS FLX Titanium, GS Junior (Roche) and the PGM system—personal genome machine (Ion Torrent), for example.

A device wherein capture molecules are bound to the separation and/or cover is particularly preferred. Such a device is advantageous because two arrays can be produced by one method.

In another preferred embodiment, the invention relates in particular to a master array produced by the method according to the invention.

The master array comprises in particular
i) a solid phase with at least one, preferably multiple compartments, wherein capture molecules are bound to the surface of the solid phase, preferably the compartments, and wherein
j) amplification products and/or derivatives of an amplification reaction are bound to the capture molecules.

It is advantageous that reusable master arrays can be generated by the method according to the invention for the production of DNA, RNA and protein microarrays. Through the choice of the sample fragments and the reaction mixture, which in the case of protein microarrays is also referred to as the derivatization mix, there is free choice about which array is to be generated. A multiwell array produced by the method described here and containing immobilized amplification products having local resolution on sample fragments can serve as a model for a copy reaction facilitates the production of additional master arrays.

Also preferable is a master array produced by the method according to the invention, comprising separation and/or coverage, wherein capture molecules are bound to the separation and/or to the cover and amplification products and/or derivatives of an amplification reaction are bound to the capture molecules.

In a preferred embodiment in which the capture molecules are not only bound in the structured solid phase but are also present on the cover with which the array is sealed during the reaction, the amplification products are immobilized on the cover and on the solid phase while retaining the spatial distribution. Preferably two master arrays are generated by this method. Firstly, a multiwell array for performing an initial sequencing reaction which can then be used for the production of DNA, RNA and protein microarrays, and secondly, a planar DNA master array with which additional DNA microarrays can be generated. By means of a hybridization reaction, a primer with a free 3' end is bound here to the amplification products situated at the surface and then lengthened by means of a reaction mixture, preferably containing a Pfu polymerase. Since the primer has a reactive group at its 5' end, the array can be brought into contact with a solid phase or a liquid phase which reacts with the groups. After the reaction and after removing the solidified liquid phase and/or solid phase under denaturing conditions, the initial DNA master array still contains single-stranded DNA but the second substrate contains the mating strand created by an amplification system. By using this method, one is capable of producing high-quality DNA microarrays, which may contain very long DNA sequences in comparison with the prior art (preferably >>200 nucleotides), which are of a very high quality because a Pfu polymerase with a proof-reading function incorporates only one incorrect nucleotide per $10^6$ nucleotides.

The master array may preferably be used to produce DNA, RNA or protein microarrays and/or for the sequencing reaction. The multiwell array in which amplification products of a sample fragment are present in some or more cavities may be available for different derivatizations, analyses or reactions for example as a reusable master array for the production of DNA, RNA or protein microarrays.

In addition, the master array may serve for a sequencing reaction. Derivatization comprises in particular the degradation, expansion or transformation of amplification products or additional molecules which are bound to amplification products or split off from them and again amplification of amplification products.

The master array may preferably be used for simultaneous amplification of different sample fragments in separate compartments. The sample fragments are preferably produced/prepared according to emPCR. To do so, the sample to be analyzed/amplified is preferably fragmented and one adapter each is coupled to the ends of each sample fragment. A solid phase surface is coated with the capture molecules and is structured in such a way that the surface is subdivided into a plurality of separate and sealed-off individual components by means of a suitable process management. Before creating or sealing the individual compartments, it is preferable to introduce both sample fragments and a reaction mix into the individual compartments. These components may be introduced either simultaneously or sequentially. Thus, an independent amplification reaction of the sample fragments may take place in each individual compartment due the reaction mixture and the amplification step. It is preferable that the amplification product is immobilized on capture molecules in regions of the individual compartment during or after the amplification. This creates an immobilized spatial distribution of the amplification products which corresponds to the original distribution of sample fragments.

The distribution pattern thus created is referred to in the sense of this invention in particular as a master array. The master array makes available subsequent derivatizations, analyses or reactions may be used for sequencing the sample fragments in particular.

In another preferred embodiment, the invention relates to a kit for amplification of sample fragments and/or for production of an array, comprising
k) a solid phase with at least one preferably multiple compartments, wherein capture molecules are bound to the surface of the solid phase, preferably the compartments,
l) a separation and/or cover and
m) at least one reaction mixture.

Furthermore, the kit is preferable wherein capture molecules are bound to the separation and/or to the cover.

It was completely surprising that a kit with which the method according to the invention could be performed could be produced. It was not to be expected that the solid phase could be stored in the long term with the bound capture molecules without any loss of binding function by the capture molecules. This became possible for the first time through the introduction of the compartments. The kit according to the invention can thus be stored for a long period of time and therefore makes it much easier to perform the method according to the invention.

EXAMPLES

The invention will now be described on the basis of an exemplary embodiment and the accompanying drawings.

The examples and illustrations are preferred embodiment variants which do not restrict the invention. The advantages that are described have also been demonstrated for the other embodiment variants mentioned and apply not only to the concrete example. The figures show:

FIG. 1 Detail of a multiwell array
FIG. 2 Preferred geometric embodiments of cavities
FIG. 3 Additional geometric embodiments of cavities
FIG. 4 Preferred capture molecules with their orientation
FIG. 5 Preferred adaptors
FIG. 6 Preferred device
FIG. 7 Additional preferred device
FIG. 8 Preferred evaluation
FIG. 9 Exemplary experimental results of a solid phase PCR
FIG. 10 Exemplary experimental results with signals of filled cavities
FIG. 11 Cover of multiwell array after the reaction 30

Figure 1:
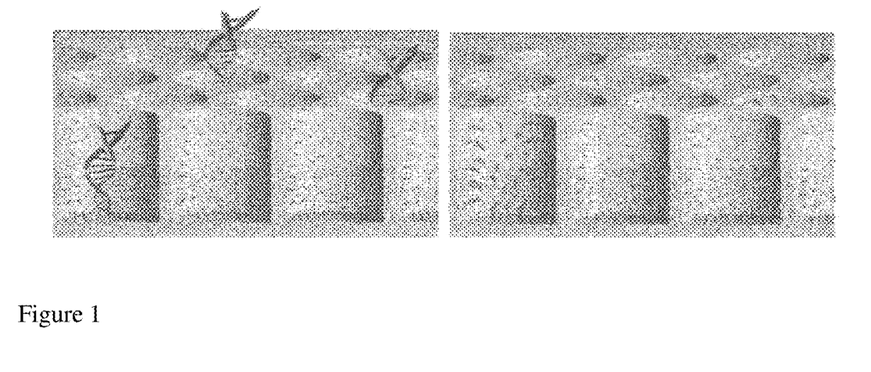

FIG. 1 shows a schematic detail of a multiwell array having a few cavities. All the cavities are coated with capture molecules. An amplification mix with sample fragments is introduced (at the left) and the cavities are closed. After amplification, the respective cavities are coated with amplification products (at the right).

Figure 2:
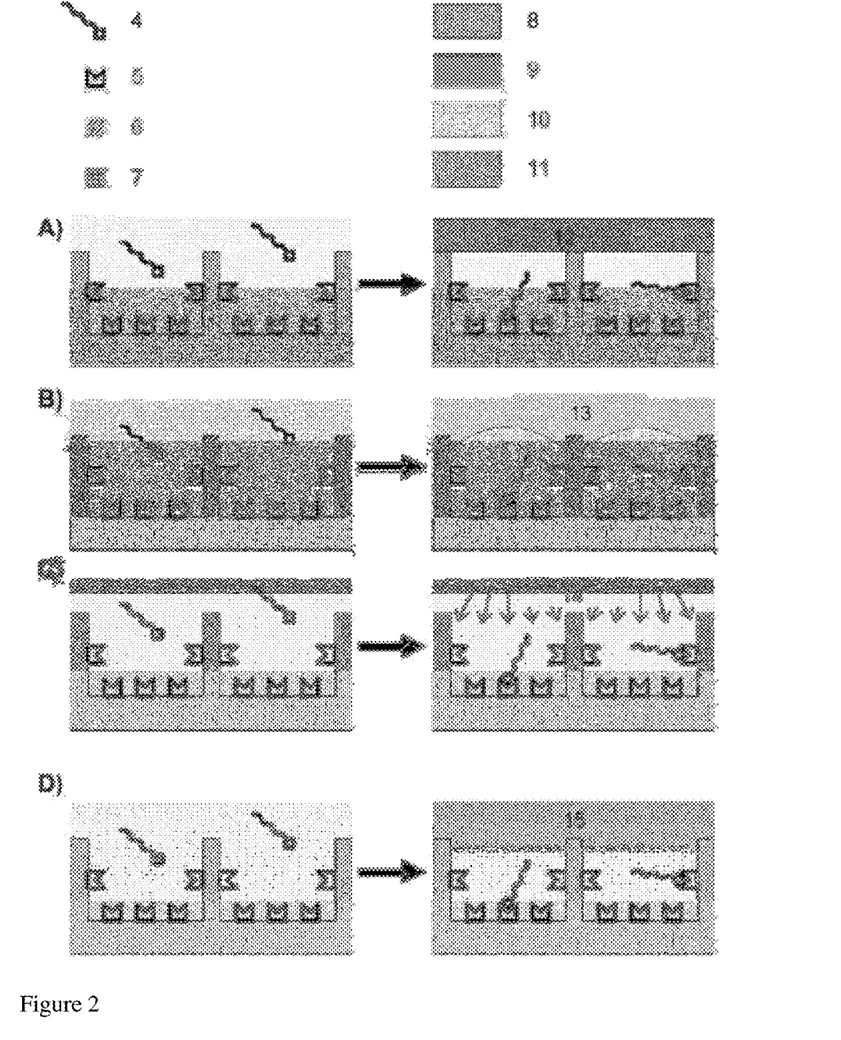

FIG. 2 shows one possible diagram of the different geometric embodiments for creating the compartmentalization for the subsequent amplification. The filled basic state is shown along with how the individual regions are shielded with respect to one another. The main interpretation is cavities (A) which are sealed with a cover. However, the cavities may also be separated from one another with oil (B), fields, in particular electric fields or by temperature (C) or a phase transition material (D).

Figure 3:
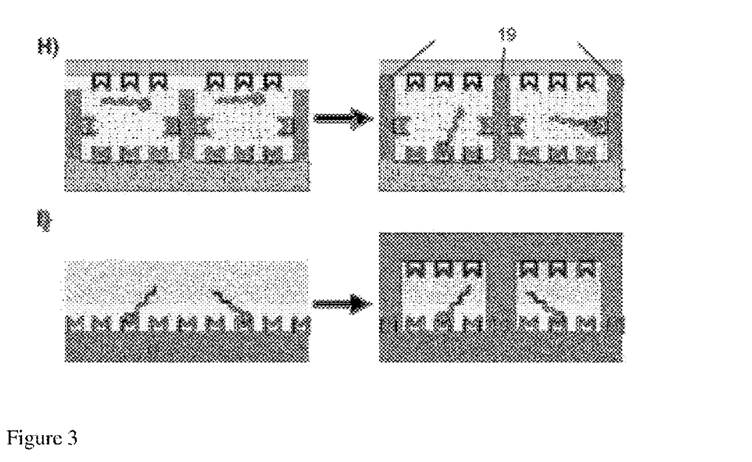

FIG. 3, like FIG. 2, shows one possible diagram of the different geometric design shapes for creating the compartmentalization for the subsequent amplification. Additional interpretations include all the structures capable of digital PCR, which are additionally coated with capture molecules (E). The sample fragments are first brought to a planar surface with capture molecules in an inverted design (F) and then are covered with a multiwell array. This is an inversion of a filling process, but it has the advantage that samples can also be enriched with highly diluted sample fragments on the planar surface. Direct filling thus could not be performed because of the excessive dilution and/or too few cavities could be filled with a sample fragment. The cavity is formed at the moment of closure. Version F may also be used to copy DNA from microarrays into a multiwell array.

Figure 4:
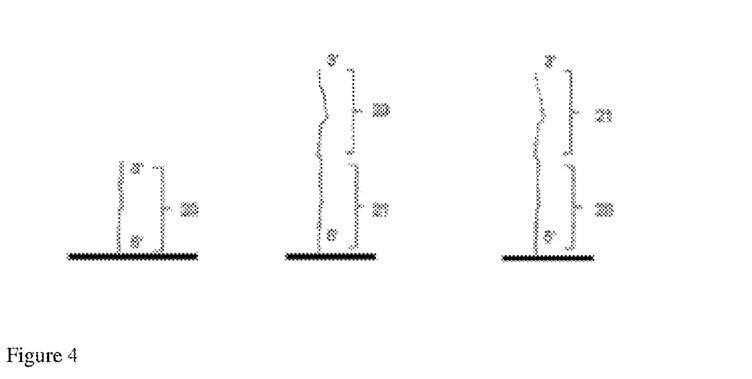

FIG. 4 shows different possibilities for capture molecules with their orientation.

Figure 5:
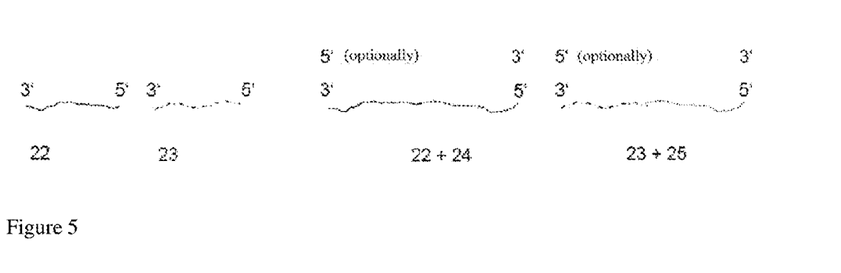

FIG. 5 shows possible embodiments of the adapters.

Figure 6:
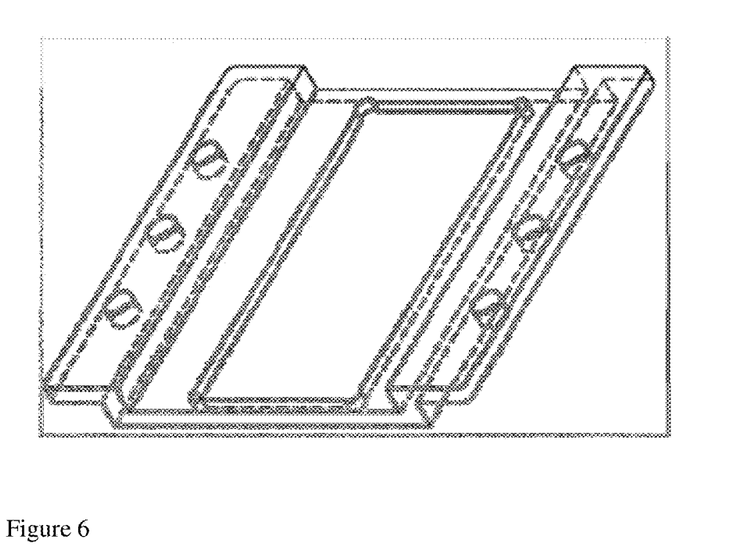

FIG. 6 shows a possible device/cassette for amplification and/or sequencing according to the invention.

Figure 7:
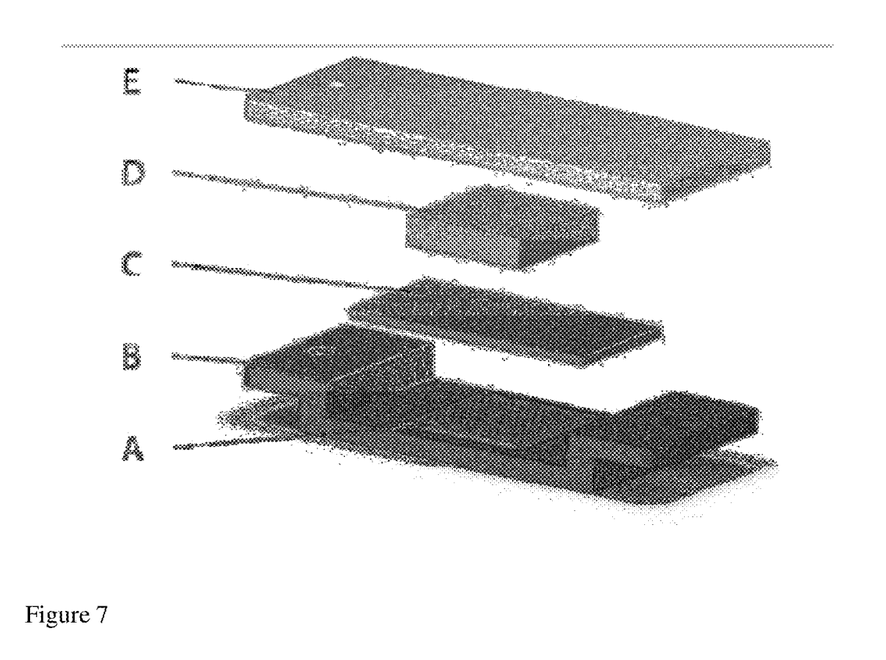

FIG. 7 shows an exploded diagram of a preferred device for the reaction of the multiwell array (A) in the recess of a cup holder (B), cover (C), 3 mm thick elastic ram (D), clamping cover (E). To introduce the amplification mix into the array by centrifugation, parts C through D are replaced by a filling device which reaches a 150 µm tall microfluidic chamber.

Figure 8:
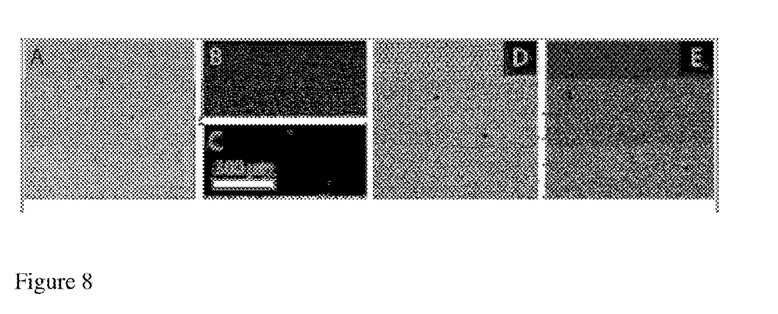

FIG. 8 shows one possible evaluation of a reaction in a multiwell array with a well volume of 19 picoliters. Figures (B) through (E) show the scans of pigmented covers after the reaction. Figure (A) shows a micrograph of a multiwell array. Figure (B) shows a specificity check. In this case, a capture molecule that is not complementary to the sequence of the DNA fragment has been immobilized, so no positive signals are generated. Figure (C) shows a no-DNA fragment check. Here again, no signals are generated. This result shows that a signal is also generated in the case of the presence of a DNA fragment. Figure (D) shows the signals of a cover in which hybridization has been used to visualize the reaction. This result shows that the correct sequence of the DNA fragments was in fact also bound to the capture molecules. In Figure (E) the surface-bound PCR product was bound by coupling streptavidine-Cy5 to the biotin molecules incorporated during the reaction, and the reaction was visualized.

Figure 9:
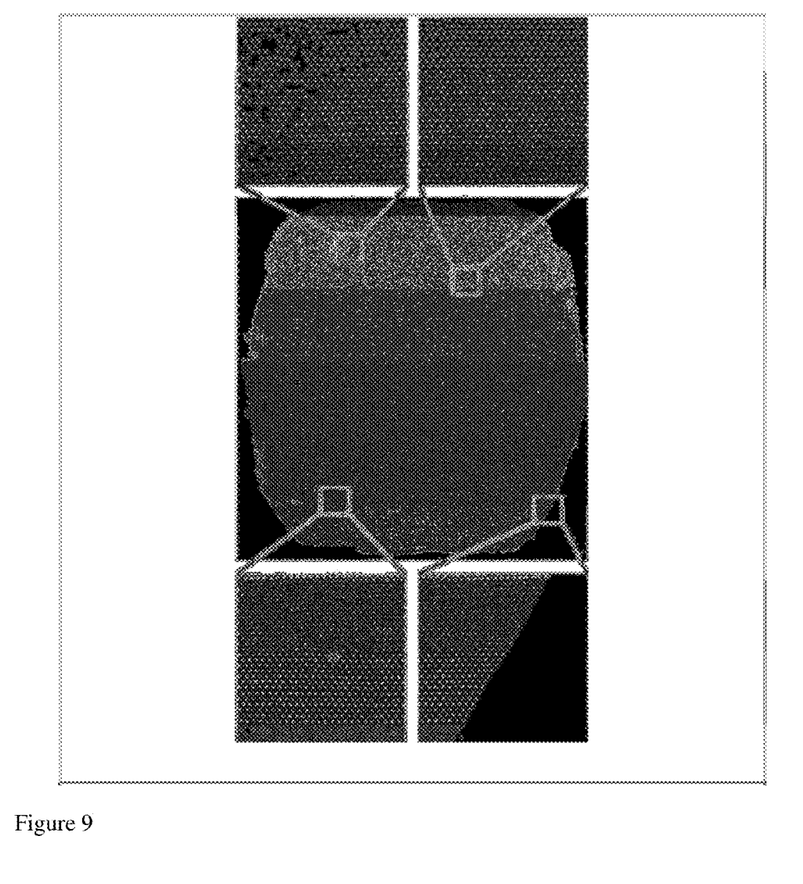

FIG. 9 shows one possible implementation of a reaction in 110,000 19-picoliter wells. In 99.18% of all wells (109, 101 signals), the PCR products were bound to the capture molecules by means of the mechanism of solid-phase PCR. This result shows that with this system, the reaction can even be performed in areas of >1 cm$^2$.

Figure 10:
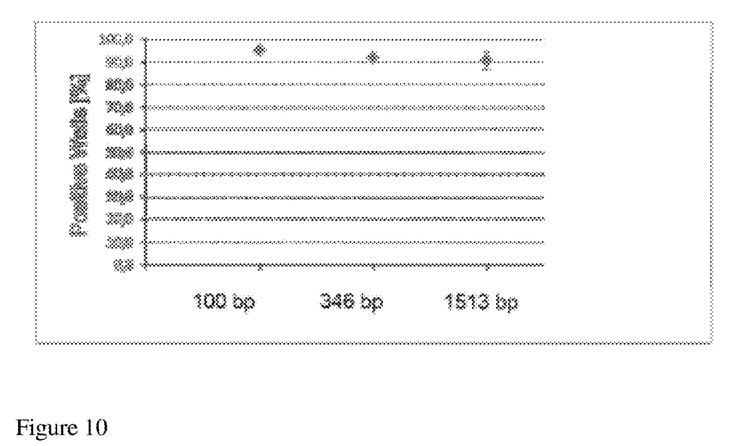

FIG. 10 shows, for example, a test for which DNA fragments of the length 100 bp, 346 bp and 1513 bp (base pairs) were used and stained with streptavidine-Cy5 after the reaction. The number of DNA fragments per well was calculated. The graph shows the number of positive signals measured by the totality of all the filled cavities (total of 10,000 wells, area 10 mm$^2$) as a function of the length of the DNA fragments. For the 100 bp DNA fragment, 95.3±1.8% positive signals were counted, for the 346 bp DNA fragment 92.1±1.9% positive signals were counted and for the 1513 bp DNA fragment 90.9±3.5% positive signals were counted. This shows that with this system it is also possible to amplify and immobilize DNA fragments >>1000 bp, which is an interesting feature in comparison with the limitations of emPCR.

Figure 11:
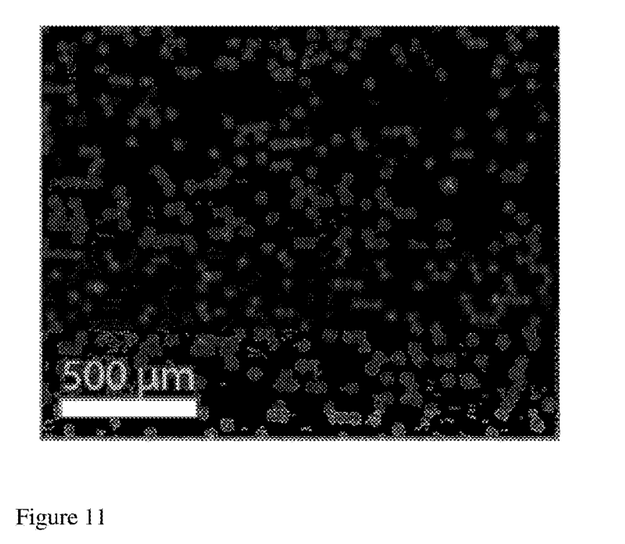

FIG. 11 shows, for example, a cover pigmented with streptavidine-Cy5 after a reaction in a multiwell array. The amplification mix contained 0.025 DNA fragments per well. The cover shows a pattern of discrete signals originating from wells in which a DNA fragment was present. This shows that a PCR product based on a single DNA fragment can be generated and, while retaining the spatial distribution, bound to immobilized capture molecules and visualized.

Example 1

Essential Sequence of the Method According to the Invention

In the first step a reaction mixture containing a defined amount of sample fragments is used. The concentration of the sample fragments is usually adjusted so that there is less than one sample fragment per volume of a cavity. The mixture is then introduced into a multiwell array whose surface is coated with capture molecules. By closing (covering) the microcavities, these are isolated from one another, so that an independent amplification reaction can take place in each cavity. The amplification products are usually bound by an adapter to the capture molecules located at the surface. Thus the inside of each cavity into which a sample fragment has been introduced is coated with the corresponding amplification products. The result is a spatially clearly defined and mutually delimited arrangement of amplification products which corresponds to the original distribution of the individual sample fragments.

Example 2

According to the following procedure, the capture molecules are applied to the cover, in particular the hybrid cover, which may consist of very thin layer (approx. 5 µm) PDMS on a glass carrier. Preferably there is first a treatment with an oxygen plasma (40 kHz generator, 100 watt power, 1 minute treatment duration) to generate hydroxide groups. In the next step, the aminosilane APTES can be bound to this (5% 3-aminopropyl-triethoxysilane (APTES), 5% DI water, 90% ethanol, reaction overnight at room temperature). Then the homobifunctional linker 1,4-phenylene diisothiocyanate (PDITC) is preferably bound to the amino groups now at the surface (0.15 g PDITC, 5 mL pyridine, 45 mL dimethyl formamide (DMF)). Next a modified ssDNA sequence can be bound as a capture molecule in particular (in 150 mM sodium phosphate buffer, pH 8.3, reaction time: overnight at room temperature). This contains in particular an amino linker at the 5' end, followed by a six-part carbon chain (C6), followed by 10 thymines. Then the actual DNA sequence of the DNA capture molecule follows. The amplification mix preferably contains 30 U HotStar Taq Plus, 1× reaction buffer, 1.5 mM $MgCl_2$, 300 µM of each dATP, dGTP, dCTP, 225 µM dTTP, 75 µM biotin-dUTP, 0.5% BSA, 0.05% Tween 80, 0.125 µM forward primer 5'-CTG AGC GGG CTG GCA-3' (SEQ ID NO: 1) and 1000 µM reverse primer 5'-GCC TCC CTC GCG CCA TCA G-3' (SEQ ID NO: 2) and between 0 and 20 copies of a DNA fragment (pTYB1 plasmid).

The aforementioned components are topped off with high purity DNAse/RNAse-free double-distilled water to a total of 16 µL. The reaction mixture is stored on ice until the multiwell arrays have been filled. A filling device for bringing the amplification mix into the array is partially identical to that from FIG. 7. The multiwell array is preferably cut out of the 13×13 $mm^2$ pieces into a Pico Titer Plate (Roche Diagnostics) (FIG. 7A).

The array is placed in the recess in the filling device (FIG. 7B), whereupon a 500 µm thick structured rubber lip is preferably placed there. Next, a microstructured filling cover, for example, can be secured on top of that using two M3 screws, each filling cover having an inlet and an outlet. Next 16 µL amplification mix can be introduced into the chamber. The entire filling device is placed on an oscillating rotor of a centrifuge (Multifuge 3SR Plus, Heraeus, VWR, Bruchsal, Germany) and centrifuged for 2 minutes at 2200 rpm.

After centrifugation, the filled array is covered with a cover coated with capture molecules (FIG. 7C). Then a rubber stamp is placed on top (FIG. 7D) and next a clamping cover (FIG. 7E), which is then screwed in place using two M3 screws. The reaction device is preferably stored at room temperature (1≤t≤10 minutes) before transferring the mixture to a Slidecycler (peqStar in situ, PEQLAB Biotechnologie). After the amplification reaction, in particular PCR, the device is dismantled and all the parts, except for the cover, are decontaminated for at least 1 hour, preferably in DNA Exitus Plus (AppliChem). The surface-bound product, preferably the PCR product, can then be detected by reaction with streptavidine-Cy5 in particular (5 µg·$mL^{-1}$ strept-avidine-Cy5 in 100 mM sodium phosphate buffer (disodium hydrogen phosphate dihydrate and sodium dihydrogen phosphate monohydrate, pH=7.2, 0.1% Tween 80, for 5 minutes at room temperature) or a hybridization reaction (0.1 µM of the hybridization probe in 5×SSC, 50% formamide 0.1%, reaction time: 12 h≤5≤16 h at 42° C.)).

Washed covers can be scanned in the InnoScan 710 scanner from Innopsys, for example. Results of such a reaction are shown in FIGS. 8-11 as an example. The PCR product here was bound to the capture molecules on a cover and then visualized by the respective method. Twenty molecules per well were introduced into the array in all reactions, except in FIG. 11.

LIST OF REFERENCE NUMERALS

4 Sample fragment
5 Capture molecule
6 Hydrophobic surface
7 Hydrophilic surface
8 Surface 1
9 Surface 2
10 Aqueous phase
11 Oil phase
12 Cover
13 Oil
14 Force field
15 Phase transition→solid
19 Valve circuit
20 Capture molecule
21 Additional nucleic acid sequence
22 Adaptor 1
23 Adaptor 2
24 Sequence 1
25 Sequence 2

The invention claimed is:

1. A method for amplifying more than one sample fragment, comprising:
   a) supplying a solid phase with a microstructure, wherein the microstructure subdivides the solid phase so that several compartments are formed, and wherein capture molecules are attached to surfaces in the compartments,
   b) introducing exactly one type of sample fragment into each of the several compartments, wherein each of the sample fragments has an adapters on one or both ends, wherein the adapters have a uniform sequence with a length of 1 to 500 nucleotides and are primers or have a binding site for RNA polymerase or a cell free expression system,
   c) introducing a reaction mixture for amplification into the several compartments,
   d) separating and/or covering the individual compartments to obtain sealed compartments, and
   e) amplifying each sample fragment of said sample fragments independently in the corresponding sealed compartment to obtain an amplification product for each of the sample fragments in each of the compartments,
   f) wherein the amplification products generated by the amplifying in (e) are immobilized on the capture molecules attached to the surfaces in each of the compartments and are subsequently analyzed, sequenced and/or derivatized.

2. The method according to claim 1, wherein the capture molecules are primers.

3. The method according to claim 1, wherein the amplification products are immobilized on the capture molecules via covalent bonds.

4. The method according to claim 1, wherein the compartments are cavities.

5. The method according to claim 1, wherein the introducing of the sample fragments and the introducing of the reaction mixture take place in one step.

6. The method according to claim 1, wherein the reaction mixture and/or the sample fragments is/are added to the compartments via centrifugation, vacuum, atomization, immersion, dip coating and/or painting the surfaces of the solid phase.

7. The method according to claim 1, wherein the surfaces of the solid phase are made of semiconducting, amorphous, crystalline and/or fibrous materials.

8. The method according to claim 1, wherein the surfaces have hydrophilic and/or hydrophobic regions and/or are structured in one or more layers as a structured surface.

9. The method according to claim 1, wherein the covering and/or separating of the compartments include oil, electric forces, phase transitions, inert regions and/or covers.

10. The method according to claim 1, wherein the capture molecules have a spacer molecule and/or comprise a chemical coupling group at one or more ends.

11. The method according to claim 1, wherein the capture molecules have a length of 1 to 1000 individual molecules.

12. The method according to claim 1, wherein the capture molecules are immobilized either directly or indirectly on the solid phase.

13. The method according to claim 1, wherein the cover comprises capture molecules.

14. The method according to claim 1, wherein the capture molecules comprise at least one binding site for sample fragments and/or amplification products.

15. The method according to claim 1, wherein the capture molecules and/or amplification products have a photoactivatable cleavage group.

16. The method according to claim 1, wherein the capture molecules have a proton binding site for an RNA polymerase or a cell-free expression system.

17. The method according to claim 1, wherein the sample fragments are nucleic acids, preferably DNA or RNA, proteins, antibodies, synthetic molecules, organic molecules and/or natural substances or have been released from cells or natural substances introduced into the compartments.

18. The method according to claim 1, wherein the sample fragments are amplified directly or indirectly via an incorporated label from DNA or RNA.

19. The method according to claim 1, wherein the sample fragments have a length of 1 to $10^{10}$ individual molecules in single-stranded or double-stranded form.

20. The method according to claim 1, wherein amplification in (e) is selected in particular from the group consisting of PCR, RPA, RCA, SDA, NASBA and LAMP.

21. The method according to claim 1, wherein the reaction mixture comprises reaction-enhancing components.

22. The method according to claim 1, wherein said amplifying does not involve an emPCR.

23. The method according to claim 2, wherein the primers are primers that are used for the amplifying in (e).

24. The method according to claim 5, wherein the sample fragments are mixed with the reaction mixture before the introducing.

25. The method according to claim 21, wherein the reaction-enhancing components are BSA, Tween and/or agarose.

26. The method of claim 11, wherein the individual molecules are bases of a DNA molecule.

* * * * *

SEQUENCE LISTING

<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: Primer

<400> SEQUENCE: 1
ctgagcgggc tggca                                                     15

<210> SEQ ID NO 2
<211> LENGTH: 19
<212> TYPE: DNA
<213> ORGANISM: Artificial Sequence
<220> FEATURE:
<223> OTHER INFORMATION: Primer

```
<400> SEQUENCE: 2
gcctccctcg cgccatcag                                               19
```